(12) United States Patent
Kuang et al.

(10) Patent No.: US 11,364,083 B2
(45) Date of Patent: Jun. 21, 2022

(54) JOINT LOCKING MECHANISM OF PASSIVE ROBOTIC ARM

(71) Applicant: SOOCHOW UNIVERSITY, Suzhou (CN)

(72) Inventors: Shaolong Kuang, Suzhou (CN); Jinzhong Li, Suzhou (CN); Li Zhang, Suzhou (CN); Andi Lin, Suzhou (CN); Liansen Sha, Suzhou (CN); Shumei Yu, Suzhou (CN); Fengfeng Zhang, Suzhou (CN); Lining Sun, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 734 days.

(21) Appl. No.: 16/320,043

(22) PCT Filed: Jan. 17, 2018

(86) PCT No.: PCT/CN2018/072932
§ 371 (c)(1),
(2) Date: Jan. 23, 2019

(87) PCT Pub. No.: WO2019/127696
PCT Pub. Date: Jul. 4, 2019

(65) Prior Publication Data
US 2021/0369358 A1    Dec. 2, 2021

(30) Foreign Application Priority Data

Dec. 29, 2017    (CN) .......................... 201711483123.5

(51) Int. Cl.
*F16D 55/02*    (2006.01)
*F16D 65/18*    (2006.01)
(Continued)

(52) U.S. Cl.
CPC ............... *A61B 34/30* (2016.02); *B25J 9/109* (2013.01); *F16D 55/02* (2013.01); *F16D 2121/16* (2013.01)

(58) Field of Classification Search
CPC .. F16D 55/28; F16D 55/30; F16D 2055/0075; F16D 65/18; F16D 2121/14;
(Continued)

(56) References Cited

U.S. PATENT DOCUMENTS 4,065,100 A * 12/1977 Walsh ...................... B66D 3/14
254/368
4,804,150 A *  2/1989 Takeuchi ............... A01K 89/02
188/166

FOREIGN PATENT DOCUMENTS

CN    201537927 U    8/2010
CN    102672718 A    9/2012
(Continued)

*Primary Examiner* — Thomas J Williams
(74) *Attorney, Agent, or Firm* — SZDC Law P.C.

(57) ABSTRACT

A joint locking mechanism of a passive robotic arm includes: an output assembly, including a joint output shaft, and a friction disk fixed to the joint output shaft; a braking assembly, including a threaded shaft arranged coaxially with the joint output shaft, a threaded sleeve threaded to the threaded shaft, a rotary disk connected fixedly to the threaded shaft, an end cap rotatable relative to the rotary disk, and a scroll spring generating a rotational force on the threaded shaft. The scroll spring has one end connected fixedly to the end cap and the other end connected to the rotary disk or the threaded shaft. The threaded sleeve is abutted tightly against the friction disk.

4 Claims, 2 Drawing Sheets

(51) Int. Cl.
    *A61B 34/30* (2016.01)
    *B25J 9/10* (2006.01)
    *F16D 121/16* (2012.01)
(58) Field of Classification Search
    CPC ............ F16D 2121/16; F16D 2125/34; F16D 2125/40; F16D 55/02; B25J 17/02; B25J 17/0241; B25J 19/0004
    USPC ................. 188/82.1, 82.2, 82.9, 83, 85, 166
    See application file for complete search history.

(56) References Cited

FOREIGN PATENT DOCUMENTS

| | | |
|---|---|---|
| CN | 202943645 U | 5/2013 |
| CN | 103622751 A | 3/2014 |
| CN | 206780439 U | 12/2017 |
| JP | 2014228040 A | 12/2014 |
| JP | 2015100878 A | 6/2015 |

* cited by examiner

JOINT LOCKING MECHANISM OF PASSIVE ROBOTIC ARM

This application is the National Phase Application of PCT/CN2018/072932, filed on Jan. 17, 2018, which claims priority to Chinese Patent Application No.: 201711483123.5, filed on Dec. 29, 2017, each of which is incorporated by reference for all purposes as if fully set forth herein.

FIELD OF THE INVENTION

The present application relates to a joint locking mechanism of a passive robotic arm.

BACKGROUND OF THE INVENTION

Recently, with the development in medical robots, medical robots have become an important branch in the field of robots and also an important research subject in the field of biomedical engineering. It has been shown that one of the major challenges for medical robots to be applied in clinics according to research and clinical practice about medical robots over the past 30 years is the safety. And in particular, the robot powered electrically, hydraulically or pneumatically is an open loop device, which interacts directly with the surgeon and patient and thus brings a lot of psychological pressure on clinicians. Therefore, it has become a focus in research and development on medical robots to develop a passive robotic arm without being driven by power for assisting in navigation surgeries or installation of a powered micro surgical robot.

An important subject in the study of passive robotic arms is to develop a joint locking mechanism. Joint locking mechanisms in the prior art are mainly hydraulic, pneumatic, electromagnetic, or mechanical. Because of bringing contamination to the operating room and the large size, hydraulic and pneumatic joint locking mechanisms' application is limited. Although electromagnetic locking mechanisms following the same principle of the power-off braking have simple structures, they can only provide limited locking force with micro size. Ideally, a joint locking mechanism based on purely mechanical locking is desired for its simple structure and operability, which will ease the psychological pressure on the surgeon. Such a joint locking mechanism does not require any special manipulating environment and will not bring contamination to the operating room.

SUMMARY OF THE INVENTION

To fulfill the need of such passive robotic arm in clinics, the present application provides a joint locking mechanism driven purely mechanically based on the principle of frictional locking.

In order to solve the technical problem mentioned above, the present application provides a joint locking mechanism of a passive robotic arm, comprising: an output assembly, including a joint output shaft, and a friction disk fixed to the joint output shaft; a braking assembly, including a threaded shaft arranged coaxially with the joint output shaft, a threaded sleeve threaded to the threaded shaft, a rotary disk connected fixedly to the threaded shaft, an end cap rotatable relative to the rotary disk, and a scroll spring generating a rotational force on the threaded shaft. The scroll spring has one end connected fixedly to the end cap and the other end connected to the rotary disk or the threaded shaft. The threaded sleeve is abutted tightly against the friction disk. When there is no external force applied, the scroll spring causes a tendency for the threaded shaft to rotate, thereby causing a tendency for the threaded sleeve fitted over the threaded shaft to move towards the joint output shaft, so that the threaded sleeve is pressed tightly on the friction disk, whereupon the friction disk under pressure causes the joint output shaft to be braked.

Preferably, the mechanism further comprises a housing, wherein the threaded sleeve is positioned within the housing, the housing is provided with a guide slot extending along the joint output shaft, and at least one positioning hole is provided in the threaded sleeve. The mechanism further comprises a pin extending through the guide slot with an end portion thereof inserted in the positioning hole. When it is rotated under an external force, the rotary disk drives the threaded shaft to rotate in a direction opposite to the tendency of rotation in a stationary state, thereby driving the threaded sleeve to move away from the friction disk along the joint output shaft so as to release the friction disk and allow the joint output shaft to start rotating. When the external force is removed from the rotary disk, a rotational force is applied to the threaded shaft by the scroll spring, causing the threaded shaft to rotate in an opposite direction and drive the threaded sleeve to move towards the friction disk along the joint output shaft and be pressed tightly against the friction disk again, so that the joint output shaft is braked. In this process, due to the pin, the threaded sleeve can only move back and forth along the length of the guide slot and along the joint output shaft.

Preferably, the joint output shaft is provided with a key mounting slot. A key is mounted within the key mounting slot. The key is protruded relative to the surface of the joint output shaft. A spline is further sleeved over the joint output shaft. The friction disk is fixed to the joint output shaft via the spline. The key is used to prevent the spline from sliding relative to the joint output shaft. The spline can simplify installation and prevent the friction disk from sliding relative to the joint output shaft.

Preferably, the rotary disk is sleeved over an end portion of the threaded shaft away from the joint output shaft. The threaded sleeve is sleeved over the threaded shaft proximate to the joint output shaft. The end cap is sleeved on the threaded shaft and positioned between the rotary disk and the threaded sleeve. The scroll spring is positioned in the end cap and sleeved over the threaded shaft.

Preferably, the end cap is mounted fixedly on an end portion of the housing. The end portion of the threaded shaft away from the joint output shaft is rotatably mounted on the end cap. The joint output shaft is rotatably mounted within the housing.

The joint locking mechanism of a passive robotic arm provided by the present application is used for medical surgeries to provide joint locking. When the external force is removed from the rotary disk, a rotational force is applied to the threaded shaft by the scroll spring, causing the threaded shaft to rotate in an opposite direction and drive the threaded sleeve to move towards the friction disk along the joint output shaft and be pressed tightly against the friction disk again, so that the joint output shaft is braked. In this process, due to the pin, the threaded sleeve can only move back and forth along the length of a guide slot and along the joint output shaft.

DETAILED DESCRIPTION OF THE EMBODIMENTS

Figure 1:
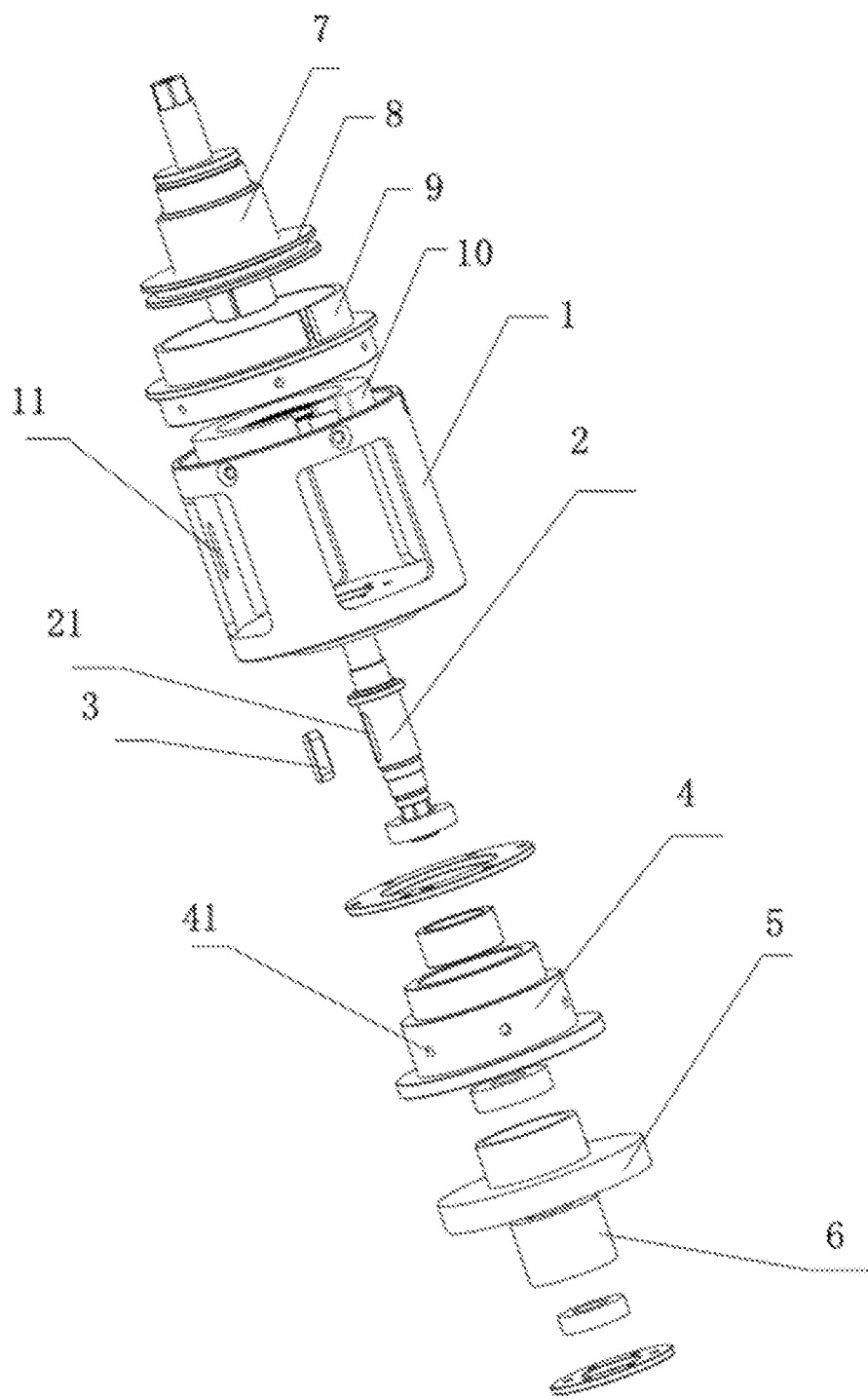
FIG. 1 is an exploded structural view of a locking mechanism according to the present application.
Figure 2:
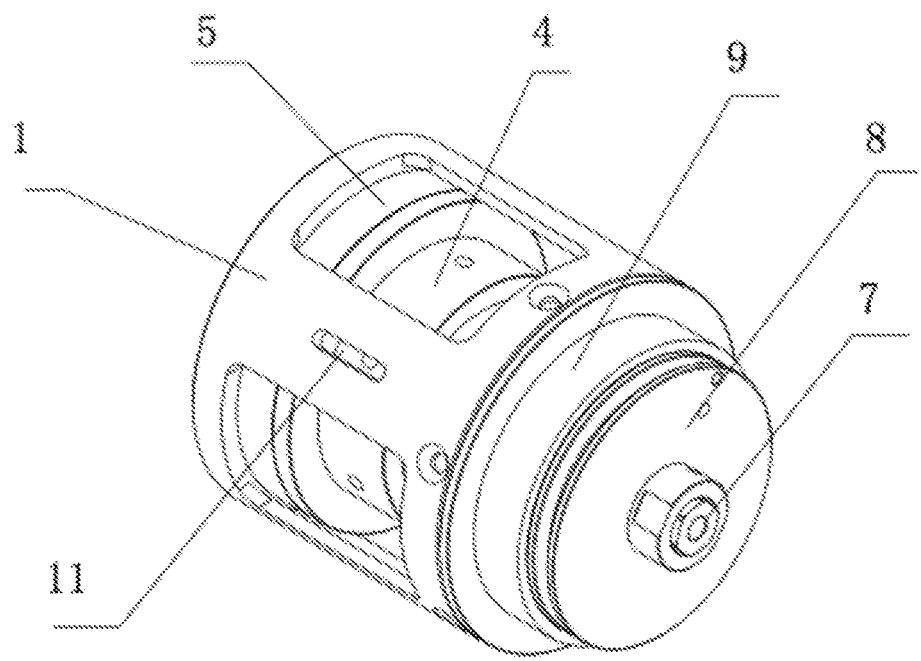
FIG. 2 is a structural view of a locking mechanism according to the present application.
Figure 3:
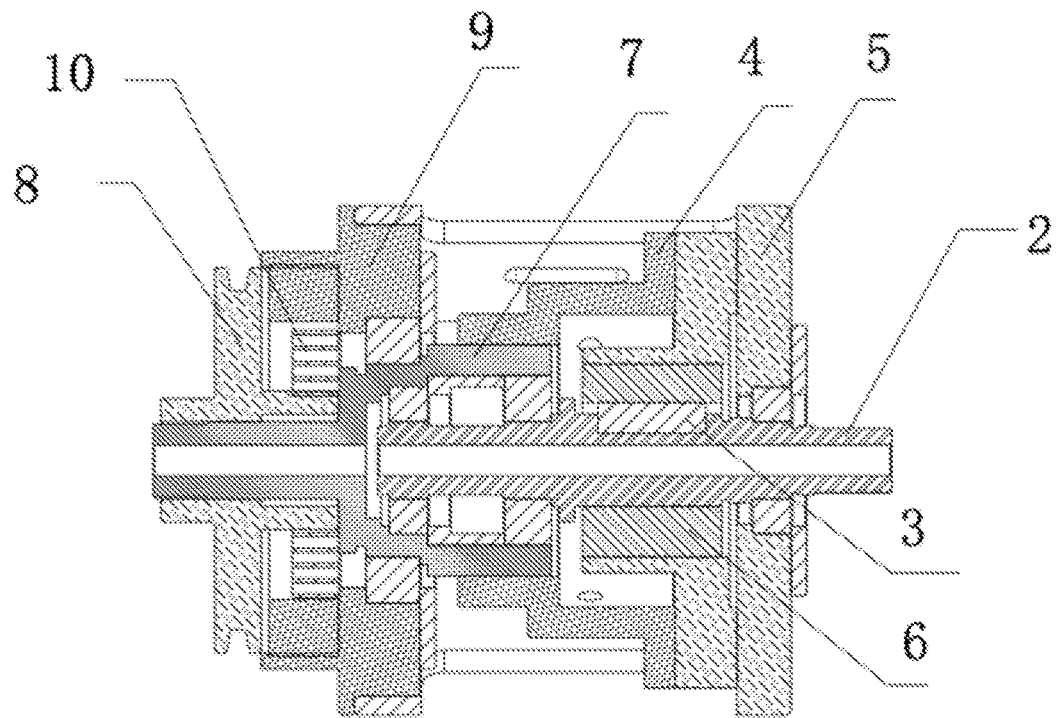
FIG. 3 is a sectional structural view of a locking mechanism according to the present application, wherein: 1. housing; 11. guide slot; 2. joint output shaft; 21. key mounting slot; 3. key; 4. threaded sleeve; 41. positioning hole; 5. friction disk; 6. spline; 7. threaded shaft; 8. rotary disk; 9. end cap; 10. scroll spring.

The present application will be further described with reference to the drawings and specific embodiments to enable those skilled in the art to have better understanding and implement the present application, but the embodiments described herein are not intended to limit the protection scope of the present application.

As shown in the drawings, the present application provides a joint locking mechanism of a passive robotic arm, comprising: an output assembly, including a joint output shaft 2, and a friction disk 5 fixed to the joint output shaft 2; a braking assembly, including a threaded shaft 7 arranged coaxially with the joint output shaft 2, a threaded sleeve 4 threaded to the threaded shaft 7, a rotary disk 8 connected fixedly to the threaded shaft 7, an end cap 9 rotatable relative to the rotary disk 8, and a scroll spring 10 generating a rotational force on the threaded shaft 7. The scroll spring 10 has one end connected fixedly to the end cap 9 and the other end connected to the rotary disk 8 or the threaded shaft 7. The threaded sleeve 4 is abutted tightly against the friction disk 5. The mechanism further comprises a housing 1. The threaded sleeve 4 is positioned within the housing 1. The housing 1 is provided with a guide slot 11 extending along the joint output shaft 2. At least one positioning hole 41 is provided in the threaded sleeve 4. The mechanism further comprises a pin extending through the guide slot 11 with an end portion thereof inserted in the positioning hole 41. The joint output shaft 2 is provided with a key mounting slot 21. A key 3 is mounted within the key mounting slot 21. The key 3 is protruded relative to the surface of the joint output shaft 2. A spline 6 is further sleeved over the joint output shaft 2. The friction disk 5 is fixed to the joint output shaft 2 via the spline 6. The key 3 is used to prevent the spline 6 from sliding relative to the joint output shaft 2. The spline 6 can simplify installation and prevent the friction disk 5 from sliding relative to the joint output shaft 2. The rotary disk 8 is sleeved over an end portion of the threaded shaft 7 away from the joint output shaft 2. The threaded sleeve 4 is sleeved over an end portion of the threaded shaft 7 proximate to the joint output shaft 2. The end cap 9 is sleeved on the threaded shaft 7 and positioned between the rotary disk 8 and the threaded sleeve 4. The scroll spring 10 is positioned in the end cap 9 and sleeved over the threaded shaft 7. The end cap 9 is mounted fixedly on an end portion of the housing 1. The end portion of the threaded shaft 7 away from the joint output shaft 2 is rotatably mounted on the end cap 9. The joint output shaft 2 is rotatably mounted within the housing 1.

The joint locking mechanism of a passive robotic arm according to the present application is operated as follows: when there is no external force applied, the scroll spring 10 causes a tendency for the threaded shaft 7 to rotate, thereby causing a tendency for the threaded sleeve 4 to move towards the joint output shaft 2, so that the threaded sleeve 4 is pressed tightly against the friction disk 5, whereupon the friction disk 5 under pressure causes the joint output shaft 2 to be braked. When it is rotated under an external force, the rotary disk 8 drives the threaded shaft 7 to rotate in a direction opposite to the tendency of rotation in a stationary state and drives the threaded sleeve 4 to move away from the friction disk 5 along the joint output shaft 2, so as to release the friction disk 5 and allow the joint output shaft 2 to start rotating. When the external force is removed from the rotary disk 8, a rotational force is applied to the threaded shaft 7 by the scroll spring 10, causing the threaded shaft 7 to rotate in an opposite direction and drive the threaded sleeve 4 to move towards the friction disk 5 along the joint output shaft 2 and be pressed tightly against the friction disk 5 again, so that the joint output shaft 2 is braked. In this process, due to the pin, the threaded sleeve 4 can only move back and forth along the length of the guide slot and along the joint output shaft 2.

The joint locking mechanism of a passive robotic arm provided by the present application is used for medical surgeries to provide joint locking. When the external force is removed from the rotary disk 8, a rotational force is applied to the threaded shaft 7 by the scroll spring 10, causing the threaded shaft 7 to rotate in an opposite direction and drive the threaded sleeve 4 to move towards the friction disk 5 along the joint output shaft 2 and be pressed tightly against the friction disk 5 again, so that the joint output shaft 2 is braked. In this process, due to the pin, the threaded sleeve 4 is limited to only move back and forth along the length of the guide slot and along the joint output shaft 2.

The embodiments described above are merely preferred embodiments for thorough description of the application, and the scope of the application is not limited thereto. Equivalent substitutions or alterations made by those skilled in the art on the basis of this application shall fall within the scope of this application. The scope of this application is defined by the claims.

What is claimed is:

1. A joint locking mechanism of a passive robotic arm, comprising:
    an output assembly, including a joint output shaft, and a friction disk fixed to the joint output shaft;
    a braking assembly, including a threaded shaft arranged coaxially with the joint output shaft, a threaded sleeve threaded to the threaded shaft, a rotary disk connected fixedly to the threaded shaft, an end cap rotatable relative to the rotary disk, and a scroll spring generating a rotational force on the threaded shaft, in which the scroll spring has a first end connected fixedly to the end cap and a second end connected to the rotary disk or the threaded shaft, and the threaded sleeve is abutted tightly against the friction disk; and
    a housing, wherein the threaded sleeve is positioned within the housing, the housing is provided with a guide slot extending along the joint output shaft, and at least one positioning hole is provided in the threaded sleeve; the mechanism further comprising a pin extending through the guide slot with an end portion thereof inserted in the positioning hole.

2. The mechanism of claim 1, wherein the joint output shaft is provided with a key mounting slot, a key is mounted in the key mounting slot, the key is protruded relative to the surface of the joint output shaft, a spline is further sleeved over the joint output shaft, and the friction disk is fixed to the joint output shaft via the spline.

3. The mechanism of claim 1, wherein the rotary disk is sleeved over an end portion of the threaded shaft away from the joint output shaft, the threaded sleeve is sleeved over an end portion of the threaded shaft proximate to the joint output shaft, the end cap is sleeved on the threaded shaft and positioned between the rotary disk and the threaded sleeve, and the scroll spring is positioned in the end cap and sleeved over the threaded shaft.

4. The mechanism of claim 1, wherein the end cap is mounted fixedly on an end portion of the housing, the end portion of the threaded shaft away from the joint output shaft is rotatably mounted on the end cap, and the joint output shaft is rotatably mounted in the housing.

* * * * *